United States Patent [19]
Smith et al.

[11] Patent Number: 5,633,130
[45] Date of Patent: May 27, 1997

[54] BUFFER SYSTEM FOR INCREASING SEROCONVERSION EFFICIENCY

[75] Inventors: Daniel S. Smith; John C. Walker, both of Columbia, Mo.

[73] Assignee: The Curators of the University of Missouri, Columbia, Mo.

[21] Appl. No.: 303,156

[22] Filed: Sep. 8, 1994

[51] Int. Cl.$^6$ .................. C12Q 1/00; C07K 1/00; C12N 9/2440; C12P 21/04
[52] U.S. Cl. .................. 435/4; 435/269; 435/2; 435/200; 435/208; 435/69.6
[58] Field of Search .................. 435/4, 69.6, 2, 435/200, 208, 269, 18

[56] References Cited

U.S. PATENT DOCUMENTS

| | | | |
|---|---|---|---|
| 4,330,619 | 5/1982 | Goldstein | 435/2 |
| 4,407,961 | 10/1983 | Sanders | 436/67 |
| 4,427,777 | 1/1984 | Goldstein | 435/240 |
| 4,609,627 | 9/1986 | Goldstein | 435/269 |
| 4,965,203 | 10/1990 | Silbering et al. | 435/188 |

OTHER PUBLICATIONS

Adams "Adenosine 5'-triphosphate determination with phosphoglycerate kinase" in *Methods of Enzymatic Analysis*, Academic Press, New York, NY, 539–543 (1963).
Aminoff et al., "Enzymes that destroy blood group specificity" *J. Biol. Chem.* 245:1659–1660 (1970).
Bradford, *Anal Biochem.* 72:248–254 (1976).
Bryant, in *An Introduction to Immunochematology*, W.B. Sanders Philadelphia, PA, pp. 280–297 (1982).
Corchete and Guerra, *Phytochemistry* 26:927–932 (1987).
Courtois and Petek, *Methods in Enzymol.* 8:565–571 (1966).
Dacie et al., "The fragility of the red blood cells: its measurements and significance" *J. Path. Bact.* 46:341 (1938).
Dietz et al., "Colorimetric determination of serum cholinesterase and its genetic variants by the propionyl–thiocholine–dithiobis . . . " *Clin. Chem.* 19:1309–1313 (1973).
Economidou et al., "Quantitative measurements concerning A and B antigen sites" *Vox Sang.* 12:321–328 (1967).
Feinberg and Vogelstein, *Anal. Biochem.* 132:6–12 (1983).
Fong et al., *Transfusion*, 14:551–559 (1974).
Flowers and Sharon, "Glycosidases–properties and application to the study of complex carbohydrates and cell surfaces" *Adv. Enzymol.* 48:29–95 (1979).
Goldstein and Swain, *Phytochemistry* 4:185–192 (1965).
Goldstein et al., *Science* 215:168–170 (1982).
Goldstein, *Trans. Med. Rev.* 3:206–212 (1989).
Goldstein, in *Biotechnology of Blood*, pp. 75–100 (1991).
Haibach et al., "Purification and characterization of a *Coffea canephora* α–D–galactosidase isozyme" *Biochem. Biphys. Res. Comm.* 191:1564–1571 (1991).
Hanahan, "Studies on transformation of *E. coli* with plasmids" *J. Mol. bio.* 166:557–580 (1983).
Harlow et al., "Immunizing animals" in *Antibodies*, Cold Spring Harbor Laboratory, Cold Spring harbor, NY, Chap. 5. 92–135 (1988).

Harmening, in *Modern Bloodbanking and Transfusion Practices*, F.A. Davis Company, Philadelphia, PA, pp. 80–82 (1989).
Harpaz et al., "Studies on B–antigenic sites of human erythrocytes by use of coffee bean α–galactosidase" *Arch. Biochem. Biphys.* 170:676–683 (1975).
Hata et al. "Purification and characterization of N–acetyl–α–D–galactosaminidase from *Gallus domesticus*" *Biochem. Intl.* 28:77–86 (1992).
Hobbs et al., "An ELISA for blood group specific exogylcosidases" *J. Immunol. Methods.* 160:261–266 (1993).
Honda et al., "Enzymic synthesis of galactooligosaccharides by trans-glycosylation with thermostable . . . " *Pyconporus cinnabarinus Saga Daigaku Nogakuba Iho.* 69:55–61 [n/avail].
Hoskins et al., "Mucin degradation in human colon ecosystems . . . " *J. Clin. Invest.* 75:944–953 (1987).
Issit, "Forces that hold red cells apart" in *Applied Blood Group Serology*, Montgomery (Scientific Publications, Miami, Florida) pp. 35–36 (1985).
Kitahata et al. "Synthesis of 6–O–α–D–galactosyl α–cyclodextrin . . . " *Biosci. Biotechnol. Biochem.* 56:1518–1519 (1992).
Kubo "Changes in the specificity of blood groups induced by enzymes from soil fungi" *J. Forensic Sci.* 34:96–104 (1989).
Laemmli "Cleavage of structural proteins during the assembly of the head of bacteriophage T4" *Nature* 227:680–685 (1970).
Landsteiner, "Uber agglutination–serscheinungen normalen menschlichen blutes" *Klin. Wschr.* 14:1132 (1901) [n/available].
Lenny et al., in *Biotechnology of Blood* (Butterworth–Heinemann, Boston, MA) pp. 75–100 (1991). [n/a –will send upon receipt].
Lenny et al., "Group B.ertyrocytes enzymatically converted to group O survive normally in A, B, and O individuals" *Science* 245:168–170 (1982).
Lenny et al., "Single–unit transfusions of RBC enzymatically converted from group B to group O to group A and O normal volunteers" *Blood* 77:1383–1388 (1991).
Levy et al. "The α–N–acetylgalactosaminadase (A–xyme) from *Clostridium perfringens*" *Fed. Proc.* 37:1601 (1978).
Levy et al., "Purification and properties of α–N–acetylgalactosaminidase from *Clostridum perfringens*" *Biol. Chem.* 255:11737–11742 (1980).

(List continued on next page.)

Primary Examiner—James C. Housel
Assistant Examiner—Jennifer Shaver
Attorney, Agent, or Firm—Kohn & Associates

[57] ABSTRACT

A method of increasing efficiency of deantigenation of blood group epitopes on erythrocytes (seroconversion) by exoglycosidases utilizing a step of performing the deantigenation in a zwitterionic buffer. The method provides a buffer system and exoglycosidase that utilizes a twenty to one hundred fold lower total enzyme mass than the prior art methods.

7 Claims, 6 Drawing Sheets

OTHER PUBLICATIONS

Mawhinney "Simultaneous determination of n-acetylglucosamine, N-acetylgalactosamine . . . " *J. Chromatogr.* 351:91–102 (1986).

Mizutani et al., "Visual disturbances, serum glycine levels and transurethral resection of the prostate" *J. Urol.* 144:697–699 (1990).

Mollison et al., in *Blood Transfusion in Clinical Medicine.* Blackwell Scientific Publications, Oxford, England, p. 593 (1987).

Moore et al., "A modified ninhydrin reagent for the photometric determination of amino acids and related compounds" *J. Bio. Chem.* 211:907–913 (1954).

Moran and Walker, "Molecular cloning of two novel protein kinase genes from *Arabidopsis thaliana*" *Anal. Biochem.* 132:6–12 (1993).

Overbeek et al., "Cloning and nucleotide sequence of the α-galactosidase cDNA from Cyamopis tetragonoloba (guar)" *Plant Mol. Bio.* 13:541–550 (1989).

Rose et al., "Direct determination of 2,3-diphosphoglycerate" *Anal. Biochem.* 35:177–180 (1970).

Romano and Mollison, "Red cell destruction in vivo by low concentrations of IgG anti–A" *Br. J. Haematol.* 29:121–127 (1987).

Schmidt in *Immunobiology of the Erythrocyte,* Alan R. Liss, Inc., NY, pp. 251–261 (1980).

Sharon and Fibach, "Quantitative flow cytometric analysis of ABO red cell antigens" *Cytometry* 12:545–549 (1991).

Sherwood et al., "Assay of plasma glycine by HPLC with electrochemical detection in patients undergoing glycine irrigation during . . . " *Clinica Chimica Acta* 203:275–283 (1991).

Srivastava et al., "α–L–fucosidase from bull seminal plasma: its purification and acrosome reaction promoting property" *Biochem. Biophys. Res. Commun.* 137:1061–1068 (1986).

Tsuji et al., "Purification and characterization of α–L–Fucosidase from *Bacillus circulans* grown on procine gastric mucin" *J. Biochem.* 107:324–330 (1990).

Watanabe and Hakomori, "Status of blood group carbohydrate chains in ontogenesis and in oncogenesis" *J. Exp. Med.* 144, 644–653 (1976).

Yatziv et al., "Action of α–galactosidase on glycoprotein from human B–erythrocytes" *Biochem. Biophys. Res. Commun.* 45:514–518 (1971).

BUFFER SYSTEM FOR INCREASING SEROCONVERSION EFFICIENCY

TECHNICAL FIELD

The present invention relates to a purified enzyme preparation of the type used in the conversion of certain sub-types of blood type erythrocytes to type O cells to render the cells useful for transfusion therapy. More specifically, the present invention provides a novel buffer system rendering the process commercially useful.

BACKGROUND OF THE INVENTION

The A, B, and H antigens are a clinically significant blood group (Landsteiner, 1901; Mollison et al, 1987). These antigens are terminal immunodominant monosaccharides on erythrocyte membrane glycoconjugates (Harmening, 1989). High densities of these epitopes are present on erythrocyte membranes and antibodies bound to these antigens readily fix complement (Economidou, et al, 1967; Romano and Mollison, 1987). Because these epitopes are ubiquitous in nature, immuno-potent and naturally occurring, complement fixing antibodies occur in individuals lacking these antigens, and transfusion of incompatible blood results in fatal hemolytic transfusion reactions (Fong et al, 1974; Schmidt, 1980).

Complex sugar chains in glycolipids and glycoproteins have often been implicated in the growth and development of eukaryotes (Watanabe et al., 1976). In particular, complex sugar chains play an important part in the recognition of self in the immune system (Mollison et al., 1987). Exoglycosidases are enzymes which can modify carbohydrate membrane epitopes, thereby modulating the immune response (Goldstein et al., 1982). The α-D-galactosidase from *Glycine max* is an enzyme that degrades the human blood group B epitope to the less immunogenic blood group H antigen also known as blood group O (Harpaz et al., 1977).

α-D-galactosidases [EC 3.2.1.22] are a common class of exoglycosidases. Although physical properties of these enzymes differ as a group, and the physiological significance of these enzymes are not clearly established, isozymes of α-D-galactosidase are common to many plant species (Flowers et al, 1979; Corchete, et al 1987). Several investigators have studied α-D-galactosidase from Coffea (Yatziv, 1971). There are reports that several isozymes exist for the Coffea α-D-galactosidase enzyme (Courtois, 1966).

Modification of the A, B, and H antigens using exoglycosidases to hydrolyze the terminal immunodominant residue has previously been described (Tsuji et al, 1990; Levy & Aminoff, 1978; Yatziv & Flowers, 1971; Kubo, 1989). Hydrolysis of the terminal N-acetyl-α-D-galactosamine by α-N-acetyl-galactosaminidase (EC 3.2.1.49) converts blood type $A_2$ to blood type O, and similarly, hydrolysis of the terminal α-D-galactose residue by α-D-galactosidase (EC 3.2.1.22) converts blood type B to O (Yatziv & Flowers, 1971; Levy & Aminoff, 1978). An α-D-galactosidase from *Coffea canephora* has been shown to effectively convert type B erythrocytes to type O erythrocytes (Harpaz, 1975). Because type O erythrocytes are generally universally transfusable, enzymatic deantigenation would have important medical applications.

Improvements of this technology could increase the compatible blood supply while reducing waste and risk of transfusion reactions. The primary impediments to seroconversion have been the large quantities of enzyme required for deantigenation, and washing the red cell concentrates to achieve the desired pH (Goldstein, 1989). Further, the reaction needs to take place at 24° C. Standard transfusion medicine protocol requires treating erythrocytes at or below 24° C. in order to decrease the possibility of bacterial contamination and maintain cell function and survival. Therefore, it is commercially important to isolate enzymes and develop buffer systems in which efficient seroconversion can occur at 24° C.

Work by Goldstein et al., 1982, lead to the feasibility of large scale enzymatic conversion of blood type B to O erythrocytes (Lenny et al, 1982, 1991). This group used Coffea α-D-galactosidase in PCBS buffer to achieve deantigenation. These cells were transfused into individuals with anti-B antibodies and survived normally. The current problem with this application is that very high enzyme concentrations, about one to two grams of exoglycosidase per transfusable unit of red cells, are required for deantigenation (Lenny and Goldstein, 1991). The cost of this amount of enzyme is enormous and, without reduction, renders this technology impractical.

Data establishing the optimal ionic strength, pH, buffer species, or enzyme concentration for efficient deantigenation has not been published. It is presently unknown whether exoglycosidase activity can be modified to achieve more efficient hydrolysis of the B antigen in red cell concentrates.

U.S. Pat. No. 4,330,619, issued May 18, 1982; U.S. Pat. No. 4,427,777, issued Jan. 24, 1984; and U.S. Pat. No. 4,609,627, issued Sep. 2, 1986, all to Goldstein, relate to the enzymatic conversion of certain erythrocytes to type O erythrocytes. The above-mentioned U.S. Pat. Nos. 4,330, 619 and 4,427,777 disclose the conversion of B-type antigen to H-type antigens by using α-D-galactosidases from green coffee beans (*Coffea canephora*). The patent discloses the significant potential of such enzymes to be used in the conversion of type B erythrocytes to type O erythrocytes but does not provide a commercially feasible method. Additionally, other compounds such as tannins, present in α-D-galactosidase enzyme isolates from plants such as Coffea beans can potentially inhibit or impair enzyme function which provides a further disadvantage for their commercial use (Goldstein et al, 1965).

It would also be useful to have additional exoglycosidases, particularly those active at neutral pH, that could be used in the deantigenation of blood group serotypes for transfusions. However, the screening procedures currently available to undertake a survey of procaryotic species that produce exoglycosidases active at neutral pHs against blood group epitopes (Tsuji et al., 1990; Aminoff & Furukawa, 1970; Levy & Aminoff, 1980) and to characterize the resulting cells are cumbersome, time consuming and expensive to run.

For example, quantitation of red cell membrane deantigenation has been accomplished by conventional hemagglutination assays. However, hemagglutination titers are not highly sensitive and are technically cumbersome. Furthermore, a 50% decrease in antibody concentration only correlates with a one-fold change in titer. Thus, it is difficult to vary a large number of parameters and detect subtle changes in deantigenation using this assay.

A sensitive, rapid assay that could be used in deantigenation studies on native red blood cells and could be used for screening culture banks or selecting bacterial mutants that constitutively express blood group specific enzymes would be very useful. It would also be useful if the assay could be used to characterize other blood group specific exoglycosidases as well as blood group A active α-N-acetyl-galactosaminidases and blood group systems I and P which express terminal immunodominant saccharide epitopes.

Finally, for further studies of the soybean exoglycosidase and for more efficient production and supply of purified soybean α-D-galactosidase, it would be useful to have recombinant soybean α-D-galactosidase available. Cloning of the gene will allow rapid and efficient production of the enzyme.

SUMMARY OF THE INVENTION AND ADVANTAGES

According to the present invention, a method of increasing efficiency of deantigenation of blood group epitopes on erythrocytes (seroconversion) by exoglycosidases utilizing a step of performing the deantigenation in a zwitterionic buffer. The method provides a buffer system and exoglycosidase that utilizes about twenty to one hundred fold lower total enzyme mass than the prior art methods with an enzyme isolated from Coffea.

When deantigenating the ABO blood type, the method includes the steps of isolating A, B, or AB erythrocytes and suspending the isolated erythrotypes in an enhancing zwitterionic buffer. The exoglycosidase is then added and the cell suspension is incubated at 24° C. for between one and two hours and washed in phosphate buffered saline. This method provides an economically viable means for seroconversion of A and B erythrocytes to be used in transfusion thereby increasing the compatible blood supply while reducing waste and risk of transfusion reactions.

A flow cytometry assay has been developed for identifying and studying blood group specific exoglycosidases. The flow cytometry assay can be used to identify optimal deantigenation conditions with objectivity. With this assay cells from larger scale assays can be harvested and their morphology/structure and function characterized. The advantages of this assay include the use of native cells, the ability to perform large numbers simultaneously, and the ability to easily determine enzyme activity over a variety of conditions.

Finally, the present invention provides the DNA (SEQ ID No.:2) and amino acid (SEQ ID No.:4) sequences of *Glycine max* α-D-galactosidase.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
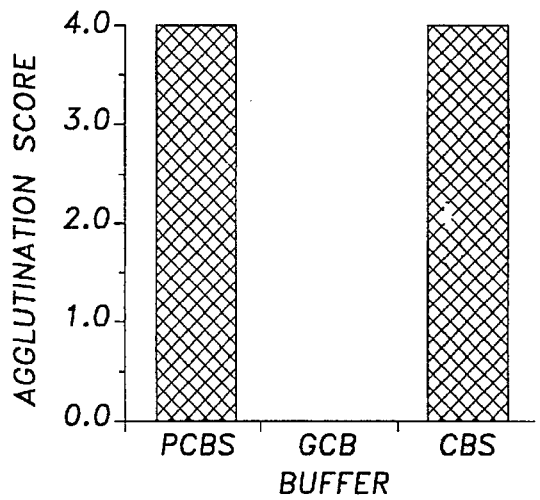
FIG. 1 is a bar graph of the agglutination score following *Glycine max* α-D-galactosidase deantigenation of type B erythrocytes in three buffers, PCBS, GCB and CBS, all data points are the means of six independent determinations.
Figure 2:
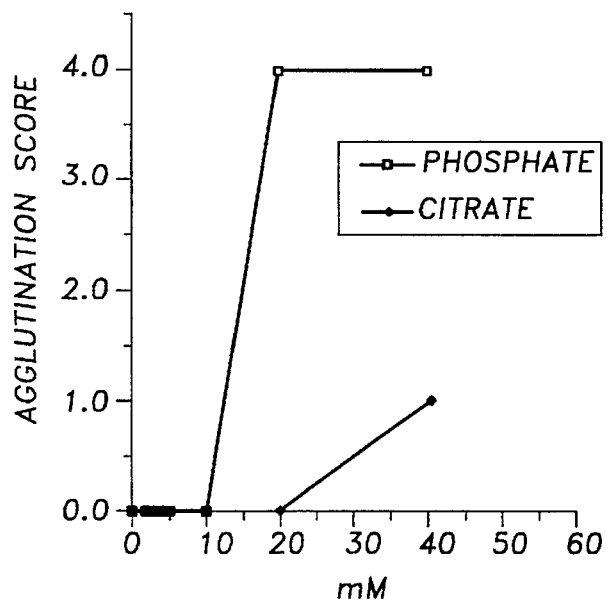
FIG. 2 is a graph of the agglutination score following *Glycine max* α-D-galactosidase deantigenation of type B erythrocytes as a function of $NaH_2PO_4$ (open square) or Na citrate (filled diamond) concentrations (0, 1.25, 2.50, 5, 10, 20, 40), all data points are the means of six independent determinations; data points initially overlap.
Figure 3:
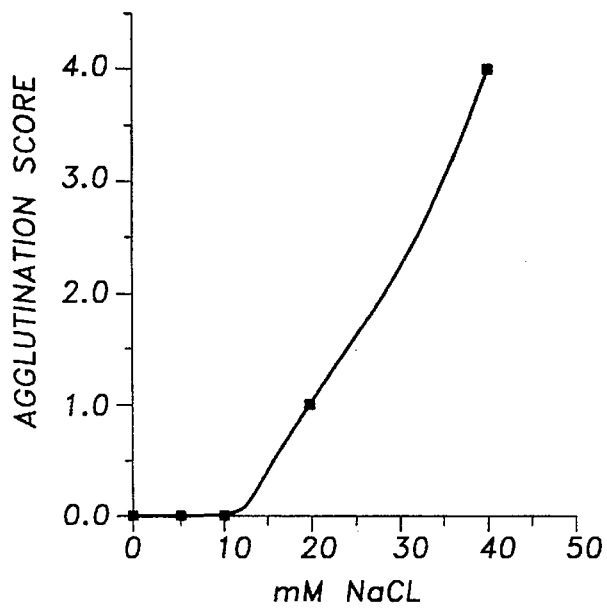
FIG. 3 is a graph of the agglutination score following *Glycine max* α-D-galactosidase deantigenation of type B erythrocytes as a function of NaCl concentration (0, 5, 10, 20, 40), all data points are the means of six independent determinations.
Figure 4:
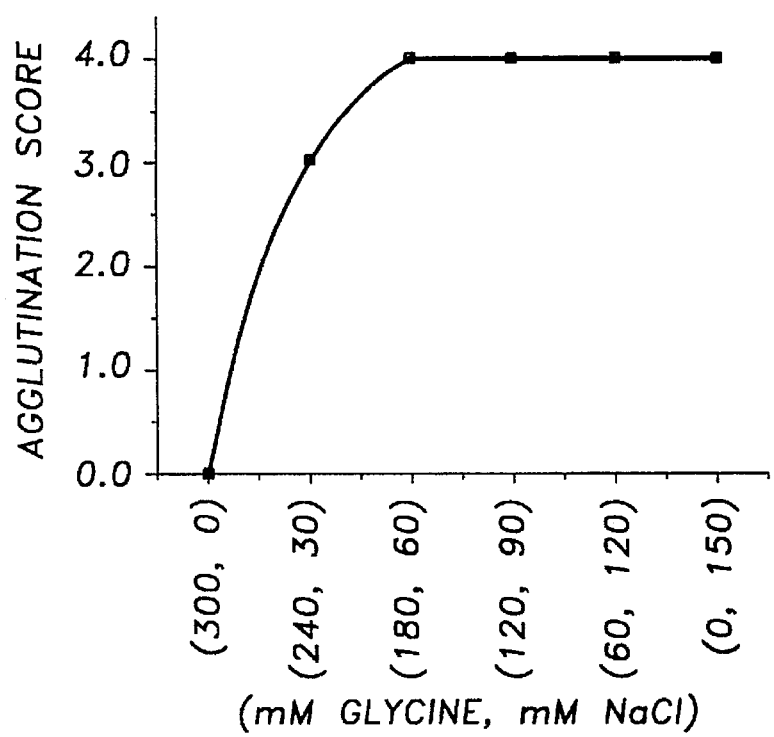
FIG. 4 is a graph of the agglutination score following *Glycine max* deantigenation of type B erythrocytes as a function of glycine and NaCl concentration (300,0), (240, 30), (180,60), (120,90), (60,120), (0,150), all data points are the mean of six independent determinations.

The present invention provides a method of increasing efficiency of deantigenation of blood group epitopes on erythrocytes, seroconversion, by exoglycosidases. Generally, the method includes a step of performing deantigenation in an enhancing buffer.

In a preferred embodiment, when deantigenating either B or A epitopes using α-D-galactosidase from *Glycine max* and *Gallus domesticus* α-N-acetyl-galactosaminidase, respectively, the method generally includes the steps of isolating A, B, and AB erythrocytes and suspending the isolated erythrocytes in a zwitterionic buffer. The appropriate exoglycosidase is then added and the cell suspension incubated at 24° C. for between one and two hours and washed in phosphate buffered saline to remove both the exoglycosidase and enhancing buffer.

Additionally other blood types with a galactose or N-acetylgalactosamine terminal group such as $P_1$ can be modified with the present invention.

The exoglycosidases are selected from the group consisting of *Glycine max* α-D-galactosidase, *Gallus domesticus* α-N-acetyl-galactosaminidase, *Phaseolus vulgaris* α-galactosidase and other multimeric eucaryotic exoglycosidases containing multiple subunits. Monomeric enzymes, i.e. an enzyme without subunits, may also be enhanced.

The zwitterionic buffer contains zwitterions selected from the group consisting of glycine, alanine, CHAPS, and zwitterions not containing additional charged groups, i.e., neutral overall charge. The glycine is used at a 220 to 440 mM concentration, in a buffer having 0.1 to 20 mM Na citrate, and 0.01 to 30 mg ml$^{-1}$ albumin at pH 5.8. In a preferred embodiment, the zwitterionic buffer consists of 5 mM Na citrate, 300mM glycine and 1 mg ml$^{-1}$ albumin at pH 5.8. In a further preferred embodiment; the albumin is human serum albumin.

In determining the enhancing buffer, the type of exoglycosidase is considered. The subclass of exoglycosidases including α-D-galactosidase from *Glycine max* (SEQ ID No.:4) and *Gallus domesticus* α-N-acetyl-galactosaminidase respond to zwitterionic buffers.

The pH of the buffer is generally effective between 5.4 and 6.4 with a pH of 5.8 as the preferred embodiment. Deantigenation was done at a hematocrit between 8% and 16%.

In a preferred embodiment, α-D-galactosidase from *Glycine max* and *Gallus domesticus* α-N-acetyl-galactosaminidase were used for deantigenation in an enhancing buffer which contained zwitterions. The optimal concentrations of the zwitterions were determined as described in Examples 2 and 3 hereinbelow. For glycine, a concentration of 220 to 440 mM was found to be optimum.

The suitability of α-D-galactosidase from *Glycine max* over Coffea α-D-galactosidase was shown by the following data. Lower concentrations of α-D-galactosidase from *Glycine max*, as low as 2.0 U ml$^{-1}$, completely removed B antigen from native erythrocytes in GCB buffer at low hematocrits in cell suspension assays. However, under similar conditions, the *Coffea canephora* enzyme activity was undetectable. Both enzymes had similar activities in the PCBS buffer, but, because the *Glycine max* enzyme has a much higher specific activity, a smaller mass of enzyme was required to achieve deantigenation in PCBS buffer.

Inhibition of enzymatic activity at physiologic ionic strength (μ approximately 0.130 to 0.145) was significant, however, isosmotic concentrations of the zwitterion glycine did not inhibit the *Glycine max* enzyme, whereas the Coffea enzyme activity was not enhanced.

With the present invention, deantigenation with *Glycine max* enzyme, at low hematocrits, can be achieved at higher pHs in the GCB buffer, closer to physiologic conditions. The active pH range of the Glycine enzyme was suitable for enzymatic conversion. The pH used in the deantigenation buffer system has been shown to provide recovery of viable, transfusable cells (Goldstein et al., 1987; Goldstein, 1989).

Glycine containing buffers enhanced enzyme activity on native erythrocyte membranes. Other zwitterions had a similar effect. It is known that glycine disrupts the ion cloud around red cell membranes reducing the zeta potential (Issit, 1985). From the soluble B trisaccharide substrate studies, it was apparent that activity in GCB was similar to PCBS. This implies that glycine must somehow alter the interaction of the *Glycine max* α-D-galactosidase with the erythrocyte membrane enhancing hydrolysis of the B epitope. This is supported by data which shows that the effect of glycine is diminished with increasing NaCl concentrations.

The safety of use of glycine in a cell preparations to be used in humans was considered. Although glycine is a known neurotransmitter, the mean residual glycine concentration measured in the final wash buffers, 2.43 μM, was below the reported physiologic concentration of glycine, median 275 μM, range 120 to 386 μM (Issit, 1985) ands therefore, would not pose a problem. Further, the present invention will not provide levels of glycine where physiologic reactions have been described (Sherwood et al, 1991; Mizutani et al, 1990).

The step of incubating requires that the enzyme be active at 24° C. The enzyme isolated from *Glycine max* was active at 24° C., only slightly less than at 37° C. Standard transfusion medicine protocol requires treating erythrocytes at or below 24° C. in order to decrease the potential of bacterial contamination and maintain cell function and survival.

In GCB buffer, red cell function was unchanged when measured by methods described hereinbelow. The only detected antigenic change was the B and P epitopes in cell phenotyping. similar results have been reported for PCBS buffer with *Coffea canephora* α-D-galactosidase (Goldstein et al, 1982).

Interestingly, cells incubated in PCBS buffer developed spicules as described by others (Goldstein, 1982). However, cells incubated in GCB, however, maintain normal cell morphology.

One of the major obstacles to seroconversion technology is the enormous quantities of enzyme required for deantigenation; approximately one to two grams of purified Coffea enzyme is required to deantigenate the B epitope from one unit of packed red blood cells (Goldstein et al, 1982; Goldstein, 1989). By using *Glycine max* α-D-galactosidase in a zwitterionic buffer, deantigenation at about a twenty to one hundred fold lower total enzyme mass can be achieved than with a purified Coffea enzyme. This buffer-enzyme combination is an economically feasible alternative to the Coffea enzyme in PCBS.

Further, purification from plants of exoglycosidases can co-isolate contaminants that are harmful and that are expensive to remove such as in Coffea extractions which contain tannins (Goldstein et al, 1965). The present invention provides the sequence of the *Glycine max* α-D-galactosidase (SEQ ID Nos:2.4) so that a purified preparation of recombinant enzyme is available.

In an additional experiment, activity of a *Gallus domesticus* enzyme on erythrocyte membranes was modified by different buffer species. Maximal hydrolysis of the A epitope on red cell membranes was seen when using a PGB buffer. This further shows that glycine alters the enzyme-membrane interaction and that zwitterionic buffers can improve enzyme efficiency in deantigenation.

Coffea α-D-galactosidase has been used in the prior art for seroconversion of B epitopes on erythrocytes, but a zwitterionic buffer was not effective in increasing its efficiency.

Applicants have developed a novel procedure (copending application U.S. Ser. No. 07/996,029 incorporated herein by reference) for the purification of the Coffea α-D-galactosidase enzyme which results in a product with a specific activity of 145.7 U mg$^{-1}$ min$^{-1}$ which is higher than the 25 U mg$^{-1}$ min$^{-1}$ value previously described by others (Haibach et al., 1991; Lenny et al, 1982). Hydrolysis can be enhanced compared to PCBS by performing hydrolysis in 10mM MES or Na citrate+140 mM NaCl at Ph 5.8. This enhancing buffer provides a two-fold increase in efficiency, MES enhancement of B epitope hydrolysis was mirrored in the soluble phase carbohydrate studies suggesting that this compound affects the enzyme rather than the erythrocyte membrane.

These findings show that increases in exoglycosidase efficiency can be achieved with changes in buffer systems.

In undertaking the above experiments, it was useful to vary a large number of parameters and detect subtle changes in deantigenation. A sensitive, rapid flow cytometry assay that can be used in deantigenation studies on native red blood cells and can be used for screening culture banks or selecting bacterial mutants that constitutively express blood group specific enzymes was developed. The method includes the steps of preparing erythrocytes in suspension and adding an exoglycosidase under a variety of buffer conditions and concentrations. Following incubation, the cells are labeled and the deantigenation efficiency monitored with a flow cytometer.

It is a useful assay that can also be used to characterize other blood group specific exoglycosidases as well as blood group A active α-N-acetyl-galactosaminidases and blood group systems I and P which express terminal immunodominant saccharide epitopes and only require the substitution of the appropriate antibodies specific for the blood group being assayed.

The flow cytometry assay of the present invention can be used to identify optimal deantigenation conditions with sensitivity and objectivity. Furthermore, cells from larger scale assays can be harvested and their morphology/structure and function characterized.

The *Coffea canephora* α-D-galactosidase currently used for deantigenation of native erythrocytes has an acidic pH optima (Kadowaki et al, 1989; Courtois & Petek, 1966). Numerous procaryotic species produce exoglycosidases active at neutral pHs against blood group epitopes (Tsuji, et al, 1990; Aminoff & Furukawa, 1970; Levy & Aminoff, 1980). Additionally, many procaryotic exoglycosidases are active against glycolipid and glycoprotein blood group epitopes and inactive against low molecular weight chromogenic substrates (Hoskins et al, 1987). More traditional assays such as mucin or glycolipid hydrolysis followed by quantitation of liberated monosaccharide are cumbersome and time consuming. The flow cytometry assay is ideal for sensitive deantigenation studies on native red blood cells and can be used for screening culture banks or selecting bacterial mutants that constitutively express blood group specific enzymes. This assay can also be used for the characterization of other blood group specific exoglycosidases as well as blood group A active α-N-acetyl-galactosaminidases and blood group systems I and P which express terminal immunodominant saccharide epitopes.

Flow cytometry assays can be employed to characterize enzymatic modification of these epitopes. The advantages of this assay include the use of native cells, the ability to perform large numbers simultaneously, and the ability to easily determine enzyme activity over a variety of conditions.

The above discussion provides a factual basis for the use of the zwitterionic buffer. The methods used with and the utility of the present invention can be shown by the following examples.

EXAMPLES

Reagents

The source of reagents is as follows: Immulon 4 flat bottom microtiter wells (Dynatech Laboratories, Chantilly, Va.), murine monoclonal anti-B and monoclonal anti-A (Ortho Diagnostics, Raritan, N.J.), goat anti-murine μ-chain specific alkaline phosphatase conjugate (Calbiochem, LaJolla, Calif.), carbohydrate substrates (Accurate Chemicals, Westbury, N.Y.), lectins (EY Laboratories, San Mateo, Calif.). Biotinylated *Ulex europaeus* type I (UEA I) and *Dolichos biflorus* (DBA) lectins were purchased from EY Laboratories, San Mateo, Calif.

Other reagents were obtained as follows: bovine serum albumin (BSA), human serum albumin (HSA) deoxycholic acid, cetylpyridinium chloride, CHAPS, Triton X-100, 2-[N-Morpholino]ethanesulfonic acid (MES), p-nitrophenyl phosphate tablets, and alkaline phosphatase conjugated avidin (Sigma Chemical Co., St. Louis, Mo.), Bradford reagent (Bio-Rad, Hercules, Calif.), BCA reagent (Pierce Chemical Company, Rockfield, Ill.). Columns for gas chromatography were purchased from Quadrex, New Haven, Conn. Solvents were purchase from Aldrich Chemical Company, Milwaukee, Wis., and distilled prior to use. Carbohydrates employed as chromatography standards were purchased from Pfanstiehl Laboratories, Inc., Waukegan, Ill. All other chemicals were purchased from Fisher Scientific, Pittsburgh, Pa.

Polyclonal antisera reacting to *Glycine max* α-D-galactosidase was prepared in rabbits by standard methodologies (Harlow & Lane, 1988). The rabbit antisera prepared to *Glycine max* lectin did not react with Glycine enzyme in an ELISA.

Volumes (0.9) of native human type erythrocytes were collected in 0.1 volumes of 3.2% Na citrate and stored at 4° C. prior to use. Diagnostic kits for ATP, 2,3 DPG, and cholinesterase were purchased from Sigma Chemical Co., St. Louis, Mo.

Enzyme Preparations

*Gallus domesticus* α-N-acetyl-galactosaminidase was purified as previously described (Hata et al, 1992).

*Coffea canephora* isozyme was purified as previously described (Haibach et al., 1991). Its mean specific activity was 145.7 U mg$^{-1}$ min$^{-1}$ and was homogeneous by SDS PAGE.

Bos α-L-fucosidase was purified by a modification of the method of Srivastava et al, 1986. Final purification of the enzyme was purified using the affinity ligand α-L-fucopyranosycamine.

*Glycine max* α-D-galactosidase was purified by a modified procedure of Harpaz et al., 1975. Enzyme activity was measured as previously described with one unit (U) defined as one μmole of substrate hydrolyzed per minute (Haibach et al, 1991. The preparations had mean specific activities in the range of 194–213 U mg$^{-1}$ min$^{-1}$ and were homogeneous by SDS PAGE according to the method of Laemmli (1970). No hemagglutinins to type A, B, or O erythrocytes were detected in the preparations.

General Methods

Protein concentration was determined by the method of Bradford (1976).

ELISA Methodology for $A_2$ Membranes

The erythrocyte membrane preparation procedure, plate coating technique, and ELISA method are described by Hobbs et al. (1993), with the only differences being the use of $A_2$ erythrocyte membranes and monoclonal anti-A. Briefly, microtiter wells were coated with $A_2$ membranes, exoglycosidase treated, probed with anti-A IgM monoclonal antibody, then developed with anti-murine μ-chain specific alkaline phosphatase conjugate. The conversion of the $A_2$ antigen to the H antigen was quantitated using the H antigen specific *Ulex europeaus* type I lectin (UEA I) as previously described, with the exception that the UEA I conjugate was diluted 1:1600 (Hobbs et al., 1993). Studies were performed on $A_1$ membranes using essentially the same procedures, however, the plates developed with anti-$A_1$ were incubated with substrate for 15 minutes.

ELISA Methodology for B Membranes

The erythrocyte membrane preparation, plate coating technique, and ELISA method used are that of Hobbs et al. (1993). Briefly, microtiter wells were coated with B Membranes, α-D-galactosidase treated, probed with IgM monoclonal antibody, then developed with anti-murine μ-chain specific alkaline phosphatase conjugate followed by p-nitrophenyl phosphate substrate.

Cell Suspension Studies

Fresh human erythrocytes were washed five times with the indicated buffer. The washed cells were diluted to the desired hematocrit in the described buffers, enzyme added, incubated at 24° C. for the determined interval, washed five times with PBS (13 mM $NaH_2PO_4$+137 mM NaCl, pH 7.4), and assayed by a conventional hemagglutination assay as previously described (Bryant, 1982). Suspensions were also observed microscopically for hemagglutination and cell morphology. Microscopic aggregates, regardless of size, were assigned a score of 0.5 agglutination units.

Red Cell Structure and Function Studies

Erythrocyte 2,3 DPG, ATP, and cholinesterase were determined as previously described (Rose & Liebowitz, 1970; Adams, 1963; Dietz et al, 1973). The MCHC (mean corpuscular hemoglobin concentration), MCV (mean corpuscular volume), MCH (mean corpuscular hemoglobin), and RDW (red cell distribution width) were determined on a Coulter STKR by standard laboratory methods. Osmotic fragilities were determined by the method of Dacie et al. (1938). Methemoglobin and $O_2$ saturation were determined on a Model 270 Ciba Corning Cooximeter. $pO_2$ and P50 values were quantitated with a Ciba Corning arterial blood gas analyzer. Phenotyping for the ABO, CDEce, Kk, $Fy^aFy^b$, $Jk^aJk^b$, MNSs, $Le^aLe^b$, and $P_1$ blood group antigens was performed as previously described (Goldstein, 1989). Glycine was quantitated in the final washed cell supernatants with a Beckman amino acid analyzer as previously described (Moore & Stein, 1954).

Soluble Carbohydrate Substrate Studies

Reactions contained X μg of substrate and 4.0 μg of enzyme in 120 μl of CBS (10 mM Na citrate +140 mM NaCl, pH 5.8), PCBS (60mM $NaH_2PO_4$+25 mM Na citrate+75 mM NaCl, pH 5.8), MBS (20 mM MES+140 mM NaCl, pH 5.8), PGB (20 mM $NaH_2PO_4$+140 mM glycine, pH 5.8), or MGB (20 mM MES+140 mM glycine, pH 5.8). Reactions were incubated at 37° C. for the indicated time and terminated by increasing the pH to 9.0 and snap freezing. Liberated N-acetyl-D-galactosamine was extracted, derivatized, and quantitated by gas chromatography as described by Mawhinney et al. (1986). Spectra for all extracted carbohydrate derivatives were obtained and verified against standards on a Kratos MS 50 S mass spectrometer interfaced with a Carlo Erba Model 4160 gas chromatograph. Mass spectra were recorded at 70 eV with an ionization current of 50 μA, a source temperature of 250° C., and a transfer temperature of 218° C.

cDNA Preparation and Sequencing

The lambda ZAP::SB cDNA library obtained from Joe Polacco (University of Missouri) was made using RNA from germinated Williamson's soybeans. Low stringency hybridization of this library was carried out in a 25% formamide buffer at 42° C., and washes were done in a low stringency wash buffer at 42° C. (Moran & Walker, 1993). High stringency hybridization of the lambda ZAP::SB cDNA library was done in a 50% formamide buffer at 42° C. (Sambrook et al, 1989), and washes were done at 65° C. in 0.1% SDS and 0.2×SSC.

Nucleotide probes were made by first purifying the DNA fragment on a 1% low melting point agarose gel (FMC) as described by Maniatis (Sambrook et al., 1989). The DNA fragment was excised from the gel and extracted with phenol. Excess agarose was precipitated by addition of 1/10 volume of 4 M LiCl/10 mM EDTA, a ten minute incubation on ice, and centrifugation at 13,200 RPM in a cold microfuge. DNA was then ethanol precipitated from the aqueous phase. The purified DNA fragments were radiolabeled with $\alpha^{32}P$ by the random primer method (Feinberg & Goldstein, 1983), and the labeled DNA was passed through a spun column (Sambrook et al., 1989) to separate the probe from unincorporated nucleotides. For hybridization, approximately $10^6$ cpm of labeled probe were used per ml of hybridization solution.

Preparative restriction digests were performed using 10 to 20 μg of DNA with 20 units of enzyme under conditions recommended by the supplier of the enzyme.

Plasmid mini and midi preps were performed by alkaline lysis according to Maniatis (Sambrook et al., 1989). DNA sequencing reactions were done with Sequenase 2.0 (USB) under conditions recommended by the manufacturer. Reactions were subjected to electrophoresis on a 6% denaturing acrylamide gel. PCR was performed using the enzyme AmpliTaq, under conditions recommended by the supplier (Cetus). The annealing step was carried out at a temperature approximately 5° C. below the lowest Tm for either primer in the reaction. PCR products were digested, purified over a LMP agarose gel, and isolated as described above for the purification of probe DNA.

Ligations were performed according to standard procedures (Sambrook et al., 1989) using T4 DNA ligase (Promega). Transformations of frozen competent cells were performed according to the method of Hanahan (1980). Electrotransformations were done according to the Bio Rad Gene Pulser manual, using approximately 100 ng plasmid DNA or one half of a standard ligation reaction. Prior to electrotransformation, DNA in the complete ligation reaction was ethanol precipitated, thoroughly washed twice with 70% ethanol, and resuspended in 5 μl of water. SK vectors were transformed in *E. coli* DH5α and the Pichia vectors were transformed into *E. coli* TOP 10 F' which was provided with the Pichia Expression Kit (Invitrogen).

The Pichia Expression Kit was used according to manufacturer's instructions and, whenever possible, its suggestions for highest efficiency and expression levels were followed. Constructs in the Pichia expression/secretion vectors pHILS1 and pPIC9 were linearized for transformation with the restriction enzymes Aat II and Tth 111I. Both vectors have unique Bgl II sites for this purpose, however when the cloned insert contains a Bgl II site it is necessary to use other enzyme sites to accomplish linearization. Transformations were done according to the recommended spheroplast method in order to maximize probability of obtaining transformants containing multiple insertions of the cloned gene of interest. Screening of His+ transformants for the desired insertion event, and small and medium-scale growth and induction were all performed according to the Invitrogen manual provided with the kit.

EXAMPLE 1

DEANTIGENATION OF B EPITOPE WITH COFFEA ENZYME

ELISA studies

Microtiter wells were coated with excellent reproducibility. Wells developed without enzyme treatment had a mean $OD_{410}$ of 1.480 and an interplate coefficient of variation of 9.92%. The binding of anti-B as a function of enzyme concentration decreased as enzyme concentration increased. Binding of the H antigen specific lectin from Ulex europaeus increased with increasing enzyme concentration demonstrating the conversion of B to H antigen.

The effect of different buffer species on Coffea enzyme activity was studied. Enzyme activity decreased with increasing buffer concentration for all buffer species tested (including Na acetate and Bis-Tris). At 50mM only MES produced a noteworthy increase in enzyme activity over PCBS. Similar effects were seen when 140 mM NaCl was buffered with MES. Upon further experimentation, it was determined that MES effectively enhanced enzymatic activity over a pH range of 4.5 to 6.0. Increasing concentrations of $Na_2SO_4$ and NaCl inhibited enzymatic activity. Enzyme activity was inhibited by NaCl concentrations greater than 50 mM. The effect of several divalent cations on enzyme activity was studied, including $CaCl_2$, $MgCl_2$, $MnCl_2$, and $ZnCl_2$. It was found these had neither inhibitory nor enhancing effects upon enzyme activity.

The effect on enzyme activity of seven different high molecular weight polymers was determined:poly-L-lysine, poly-L-glutamate, poly-L-alanine, DEAE-dextran, dextran sulfate, dextran, and polyethylene glycol. Each polymer had either an inhibitory effect or no effect at the maximal concentrations tested, 1 mg $ml^{-1}$.

The activity of the enzyme in the presence of several detergents was determined: deoxycholic acid and 1-pentanesulfonic acid, both anionic detergents, cetylpyridinium chloride, a cationic detergent, CHAPS, a zwitterionic detergent, and n-octyl-β-D-glucopyranoside, a nonionic detergent. Enzyme activity in the presence of these detergents was significantly decreased.

Coffea α-D-galactosidase activity decreased with increasing concentrations of glycine. Enzyme activity in the presence of various concentrations of galactose dehydrogenase (0 to 5.0 U $ml^{-1}$) or 2' fucosyllactose (0 to 1.0 mg $ml^{-1}$) was determined, with both compounds inhibiting enzyme activity. Enzyme treatment in the presence of a Bos α-L-fucosidase resulted in a slight increase in enzymatic activity, approximately 28% at 2.5 U $ml^{-1}$Coffea enzyme and 2 U $ml^{-1}$ Bos enzyme, over the control reactions without fucosidase.

Transglycosylation reactions have been described with eukaryotic α-D-galactosidases (Honda et al, 1990; Kitahataet al, 1992]. In an attempt to explore the possibility that reglycosylation of the B precursor, the H epitope, was occurring, galactose dehydrogenase and 2' fucosyllactose were added to reactions. Galactose dehydrogenase and NAD were used to oxidize and trap liberated galactose, whereas 2' fucosyllactose was added as an alternate galactosyl acceptor. It was apparent that neither compound enhanced the rate of hydrolysis of the B epitopes in the solid phase ELISA. Bos α-L-fucosidase was added to the reactions in an attempt to hydrolyze subterminal α1–2 fucosyl residues and thus enhance hydrolysis of the terminal α1–3 galactose residues.

Soluble carbohydrate substrate studies

Exoglycosidase activity against five carbohydrate substrates, each in 50 mM Na citrate at pH 6.0, was determined. The Coffea enzyme was more active against straight-chain substrates than against branched substrates, with the difference in hydrolysis being roughly three-fold. The enzyme readily hydrolyzed α1–3, α1–4, and α1–6 galactosyl bonds but with the substrates that the applicants used exhibited the highest activity against the α1–3 linkage. Enzyme activity against B-trisaccharide in Na citrate, MES, and PCBS was also studied. Both Na citrate and MES increased enzymatic activity over PCBS, by 55% and 15% respectively. $K_m$ studies were done using B-trisaccharide, Galα1–2Gal[Fucα1–2]β1–3GlcNAc, and melibiose in 50mM Na citrate, pH 6.0. The $K_m$ values were 2.465 mM, 3.476 mM, and 1.718 mM, respectively. $K_m$ in MBS and PCBS were performed using B-trisaccharide as substrate. The $K_m$ in MBS and PCBS were 2.951 and 1.193, respectively.

EXAMPLE 2

DEANTIGENATION OF B EPITOPE WITH GLYCINE ENZYME

Preliminary deantigenation experiments were performed in CBS (10 mM Na citrate+150 mM NaCl+1 mg $ml^{-1}$ BSA, pH 5.8), PCBS (25 mM Na citrate+60 mM Na $H_2PO_4$+75 mM NaCl+1 mg $ml^{-1}$ BSA, pH 5.8), and GCB (5 mM Na citrate+300 mM glycine+1 mg $ml^{-1}$ BSA, pH 5.8). Incubation was for two hours at 24° C. followed by washing five times with PBS, and then treated with neat monoclonal anti-B. As shown in FIG. 1, ten U $ml^{-1}$ of enzyme incubated at hematocrit of 8% erythrocytes were most efficiently deantigenated in GCB buffer. Complete deantigenation as measured by hemagglutination was achieved at various glycine concentrations ranging from 220 to 440 mM in 5 mM Na citrate buffer, pH 5.8.

Complete deantigenation as measured by hemagglutination was achieved at various glycine concentrations. Ten U $ml^{-1}$ of enzyme was incubated at hematocrit of 8% B+erythrocytes in X mM Na citrate or $NaH_2PO_4$+300 mM glycine+1 mg $ml^{-1}$ BSA, pH 5.8 where X was tested in the range of 0 to 40, for two hours at 24° C., washed five times with PBS, and treated with neat monoclonal anti-B. Interestingly, increasing citrate or phosphate concentrations in 300 mM glycine inhibited hydrolysis of the B epitope (FIG. 2). Optimal citrate concentrations for deantigenation were below 10 mM.

Also noteworthy was the inhibitory effect of increasing concentration of NaCl (FIG. 3). Ten U $ml^{-1}$ of enzyme was incubated at hematocrit of 8% B+erythrocytes in 5mM Na citrate+300mM glycine +X mM NaCl+1 mg $ml^{-1}$ BSA, pH 5.8 with X in the range of 0 to 40, for two hours at 24° C., washed five times with PBS, and treated with neat monoclonal anti-B. Above 10 mM NaCl significant hydrolysis of the B epitope was not detected in the hemagglutination assay.

When NaCl and glycine were combined at various concentrations to achieve an osmolality of 0.310, a similar inhibitory effect was observed (FIG. 4). Ten U $ml^{-1}$ of enzyme was incubated at hematocrit of 8% B+ erythrocytes in 5 mM Na citrate +X mM glycine+Y mM NaCl+1 mg $ml^{-1}$BSA, pH 5.8, where (X,Y)=(300,0), (240,30), (180,60), (120,90), (60,120), (0,150). Cells were incubated for two hours at 24° C., washed five times with PBS, and treated with neat monoclonal anti-B.

Figure 5:
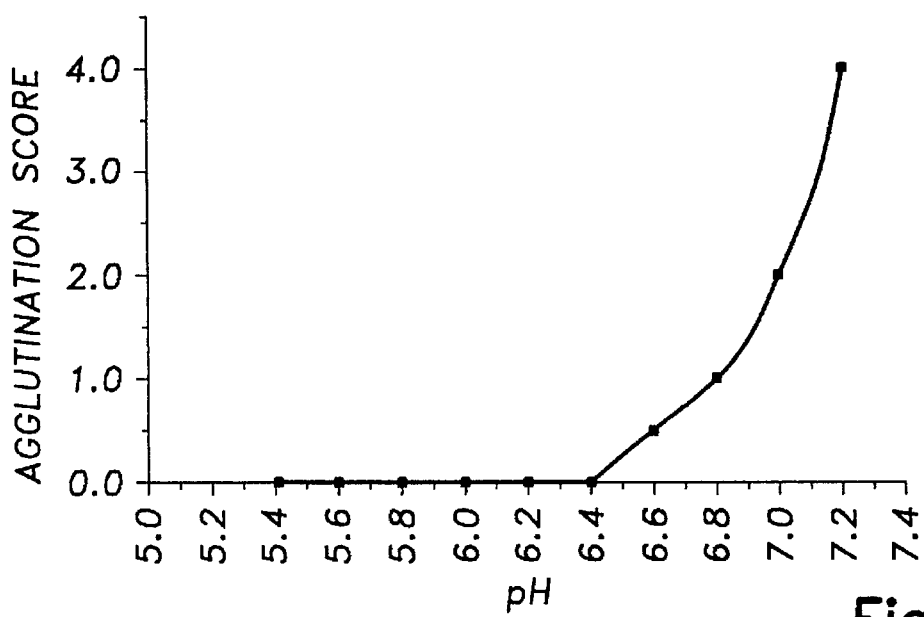
FIG. 5 is graph of the agglutination score following *Glycine max* α-D-galactosidase deantigenation of type B erythrocytes as a function of pH (5.4, 5.6, 5.8, 6.0, 6.2, 6.6, 6.8, 7.0, 7.2), all data points are the mean of six independent determinations.

Deantigenation as a function of pH is shown in FIG. 5. Deantigenation in GCB could be achieved up to a pH of 6.4 at an 8% hematocrit and enzyme concentration of 10 U ml$^{-1}$. Ten U ml$^{-1}$ of enzyme was incubated at hematocrit of 8% B+ erythrocytes in 4 mM Na citrate+4 mM NaH$_2$PO$_4$+300 mM glycine+1 mg ml$^{-1}$ BSA, pH=X, where X equals pHs of 5.4, 5.6, 5.8, 6.0, 6.2, 6.6, 7.0, and 7.2. After two hours at 24° C., the cells were washed five times with PBS and treated with neat monoclonal anti-B.

Figure 6:
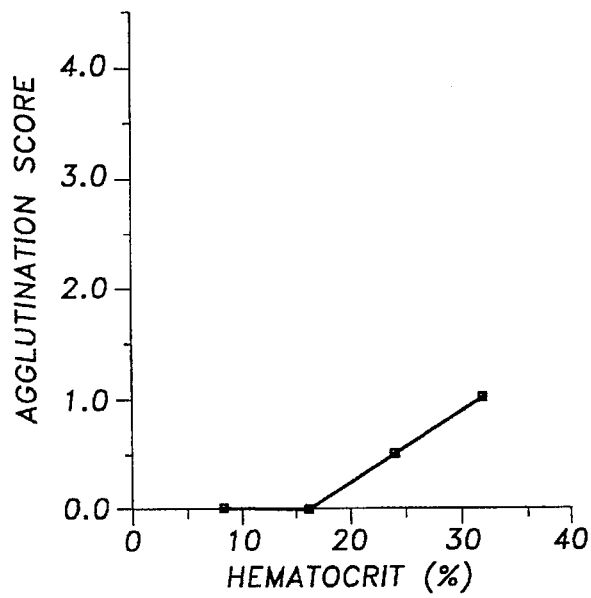
FIG. 6 is a graph of the agglutination score following *Glycine max* α-D-galactosidase deantigenation of type B erythrocytes as a function of hematocrit percentage (8,16, 24,32), all data points are the mean of six independent determinations.

The effect of increasing hematocrit at a constant enzyme concentration of 10 U ml$^{-1}$ is shown in FIG. 6. Ten U ml$^{-1}$ of enzyme was incubated at hematocrit of X% B+ erythrocytes in 5 mM Na citrate +300mM glycine+1 mg ml$^{-1}$ BSA, pH 5.8 where X%=8, 16, 24, 32 After two hours at 24° C. the cells were washed five times with PBS and treated with neat monoclonal anti-B. As shown in the graph, efficient deantigenation could be achieved at a hematocrit of 16%.

Figure 7:
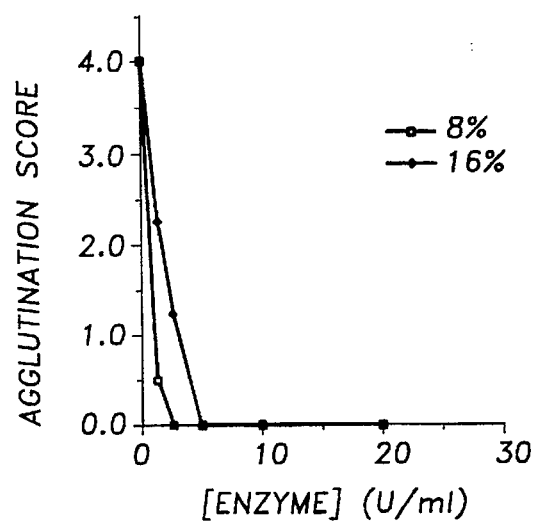
FIG. 7 is a graph of the agglutination score following *Glycine max* α-D-galactosidase deantigenation of type B erythrocytes as a function of enzyme concentration (1.25, 2.5, 5.0, 10.0, 20.0) and hematocrit of 8% (open square) or 16%, (filled diamond), all data points are the mean of six independent determinations.

FIG. 7 illustrates the effect of increasing enzyme concentration at a hematocrit of 16%. X U ml$^{-1}$ of enzyme where X=1.25, 2.5, 5.0, 10.0, 20.0 was incubated at hematocrit of 8% (open square) or 16% (filled diamond) B+ erythrocytes in 5 mM Na citrate+300 mM glycine+1 mg ml$^{-1}$ BSA, pH 5.8. After two hours at 24° C., the cells were washed five times with PBS and treated with neat monoclonal anti-B.

Figure 8:
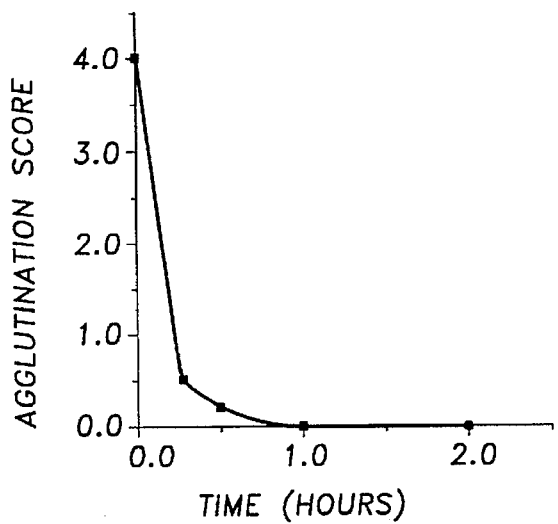
FIG. 8 is a graph of the agglutination score following *Glycine max* α-D-galactosidase deantigenation of type B erythrocytes as a function of time (0.25, 0.5, 1.0, 2.0), all data points are the mean of six independent determinations.

FIG. 8 illustrates deantigenation as a function of time. Ten U ml$^{-1}$ of enzyme was incubated at hematocrit of 8% B+ erythrocytes in 5 mM Na citrate+300 mM glycine+1 mg ml$^{-1}$ BSA, pH =5.8. After t=X hours at 24° C. where X=0.25, 0.5, 1.0, and 2.0 hours, the cells were washed five times with PBS and treated with neat monoclonal anti-B.

Also, cells could be stored in 0.32% citrate for up to six weeks and still be deantigenated under similar conditions. Experiments with *Coffea canephora* α-D-galactosidase at low enzyme concentrations, at any hematocrit, failed to achieve deantigenation in either PCBS, GCB, or CBS.

Albumin at a concentration of 1 mg ml$^{-1}$ was included in the GCB buffer because it was noted that the inclusion of albumin slightly reduced residual hemolysis. Increasing concentrations of albumin to 30 mg ml$^{-1}$ did not effect deantigenation. Identical results were obtained with either native or heat-treated human albumin. In the transfusion art, heat-treated HSA is used since it has little immunogenicity and no potential infectivity.

The effect of *Glycine max* α-D-galactosidase at a concentration of 20 U ml$^{-1}$ and a hematocrit of 16% on red cell indices (MCV, MCH, MCHC, RDW), ATP, 2,3 DPG, cholinesterase, osmotic fragility, hemolysis of red cells, carboxyhemoglobin, methemoglobin, % O$_2$ saturation, Po$_2$, and p50 were determined in PCBS and GCB. These were compared to control cells incubated in PBS. It was evident that GCB had a limited effect on increasing erythrocyte 2,3 DPG but had little effect on ATP and red cell cholinesterase, Table I.

Osmotic fragility of cells in GCB and PCBS were similar to those incubated in PBS. There was no significant change in red cell indices in either GCB or PCBS when compared to PBS incubated cells. There was no substantial change in % O$_2$ saturation, Po$_2$, and p50 in either buffer; and, furthermore, there was no substantial increase in carboxy or methemoglobin in either PCBS or GCB. In GCB, 1.53% of the red cells were hemolyzed compared to 2.16% and 1.90% in PCBS and PBS control cells, respectively.

Figure 9A:
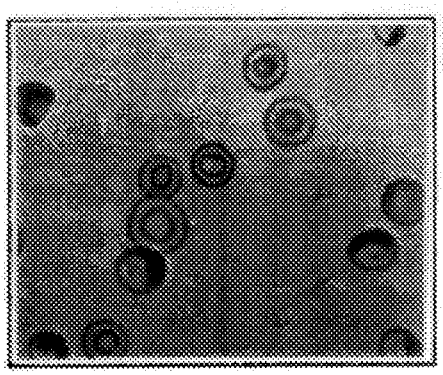
FIGS. 9A–B are photomicrographs of the morphology and agglutination of *Glycine max* α-D-galactosidase deantigenated type B erythrocytes and untreated erythrocytes, Panel A: enzyme treated erythrocytes; Panel B: untreated erythrocytes.
Figure 9B:
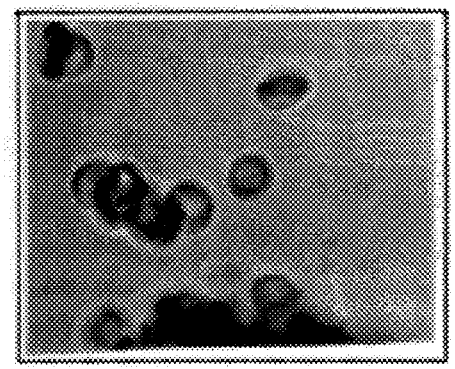

Erythrocytes incubated in GCB maintained their native morphology as shown in FIG. 9. 16% B+cells were incubated in GCB (5 Mm Na citrate+300 Mm glycine+1 mg ml$^{-1}$ BSA, Ph=5.8) with ten U ml$^{-1}$ *Glycine max* α-D-galactosidase. After two hours at 24° C., the cells were washed five times with PBS. The erythrocytes were then incubated with either neat monoclonal anti-B (enzyme treated; FIG. 9A) or a 1:128 monoclonal anti-B dilution (untreated; FIG. 9B), and photomicrographed without staining.

Additionally, extensive antigen typing was performed. The only observed change was conversion of the B to O antigen and loss of reactivity with anti-P typing sera.

EXAMPLE 3

DEANTIGENATION OF A$_2$ EPITOPE

Soluble A antigens in an ELISA using type A$_2$ erythrocyte membranes were used to study the activity of an α-N-acetyl-galactoaminidase from *Gallus domesticus*.

Results

A microtest well coating concentration of 0.4 μg ml$^{-1}$ A$_2$ erythrocyte membranes resulted in excellent reproducibility and a sufficient signal to noise ratio. The method of Hobbs et al. (1993) was used to determine primary and secondary antibody concentrations. Binding of anti-A decreased with increasing enzyme concentration while UEA I binding increased, demonstrating the conversion of the A epitope to H epitope. Also noteworthy is the fact that, at an enzyme concentration of 5 U ml$^{-1}$, hydrolysis of the A epitope from A$_2$ membranes was virtually complete. At a 1 M NaCl concentration (μ=1.01), hydrolysis of the A epitope was decreased by 64% compared to buffer without NaCl (μ=0.01). The pH optimum of the enzyme was determined to be 3.5, with a broad activity shoulder between pH 4 and 5. The enzyme still retained 60% of optimal activity at a pH of 5.8.

The effect of buffer species was also determined. 25mM MES enhanced the activity of the enzyme, increasing hydrolysis 92.6% over PCBS. Hydrolysis of the A epitope was inversely dependent upon concentration with all buffer species examined. Enzyme activity in MBS was also compared to PCBS. The MES containing buffer increased hydrolysis of N-acetyl-α-D-galactosamine by 42.9%.

The effect on enzyme activity of glycine, a zwitterion at pH 5.8 was determined. In both NaH$_2$PO$_4$ and MES buffers, glycine significantly enhanced enzyme activity. No significant inhibition was evident at glycine concentrations exceeding 300 mM in a NaH$_2$PO$_4$ buffer.

The effect of several detergents was also determined. Deoxycholic acid, cetylpyridinium chloride, and Triton X-100 (anionic, cationic, and non-ionic detergents, respectively) inhibited enzymatic activity. CHAPS, a zwitterionic detergent, enhanced enzymatic activity.

EXAMPLE 4

FLOW CYTOMETRY ASSAY

Assay Procedure

The assay is an adaptation and different application of a previously described procedure (Sharon, 1991). Briefly, 4% suspensions of human type B erythrocytes were incubated with exoglycosidase under a variety of buffer conditions and enzyme concentrations as described in the results and then washed five times with PBS (10 mM NaH$_2$PO$_4$+137 mM NaCl+2.1 mM KCl, pH 7.4). 100 μl of these 4% suspensions were incubated with 100 μl of a 1:40 dilution of monoclonal anti-B in PBS at 24° C. for 30 minutes. The cells were dispersed with a 25 gauge needle and washed five times with PBS. Next, the suspensions, 200 μl, were incubated with 5 μl of neat polyclonal goat anti-mouse μ chain specific FITC conjugate at 4° C. for 30 minutes, dispersed, and washed again five times with PBS. The cell concentrations were adjusted to $1\times10^6$ cells $ml^{-1}$, and the suspensions dispersed before cytometry.

Cells were analyzed using a EPICS 753 flow cytometer (Coulter Cytometry, Haileah, Fla.) with a 5 W argon laser tuned at 488 nm using 150 mW output. Optical alignment of the instrument was obtained using 10 μm, full-bright, fluorescent polystyrene microspheres (Coulter Immunology) with coefficients of variation kept at 2% or less. Log integral green fluorescence of 10,000 cells was collected through a 525 band-pass filter grating on forward angle light scatter versus log 90° light scatter to exclude debris. Single parameter histograms were analyzed using the STATS program on the MDADS II computer (Coulter Cytometrey). Data was obtained as percent fluorescent cells versus the logarithm of relative fluorescence. Data in the results is expressed as percent fluorescent cells as a function of the dependent variable.

Results

The 1° antibody was titrated and a 1:40 dilution was found to give optimal fluorescence with weaker agglutination than higher antibody concentrations. Fluorescence significantly decreased when less than 1 μl of the FITC conjugate was used, and 4 μl was chosen as a saturating concentration.

Figure 10:
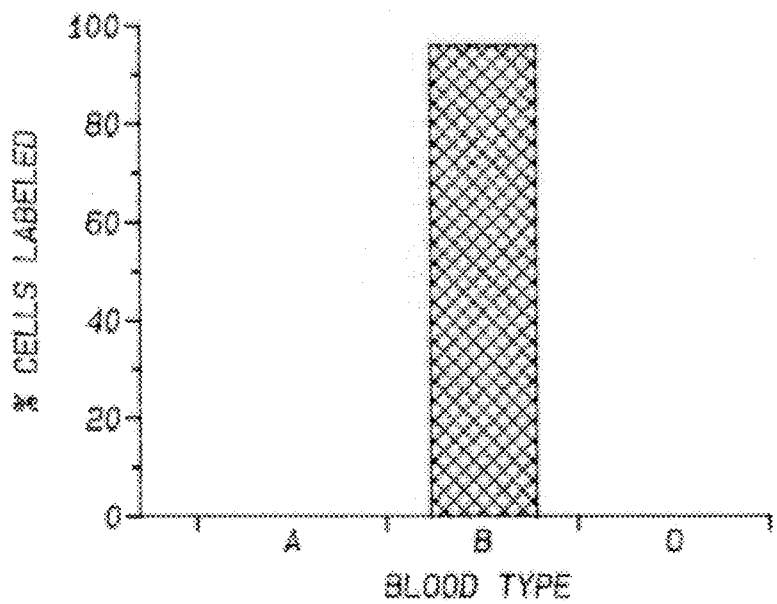
FIG. 10 is a bar graph of the reactivity of type A, B, and O erythrocytes with monoclonal anti-B, all data points are the means of three independent determinations.

FIG. 10 shows the selective reaction of monoclonal anti-B with type B cells and lack of reactivity with type A and O cells. 4% cell suspension were incubated with 1° antibody (anti-B), 2° antibody (goat anti-mouse μ chain specific FITC conjugate), and the fluorescence quantitated as described in the methods. Similar results were obtained with monoclonal anti-A reacting with only type A erythrocytes.

Figure 11:
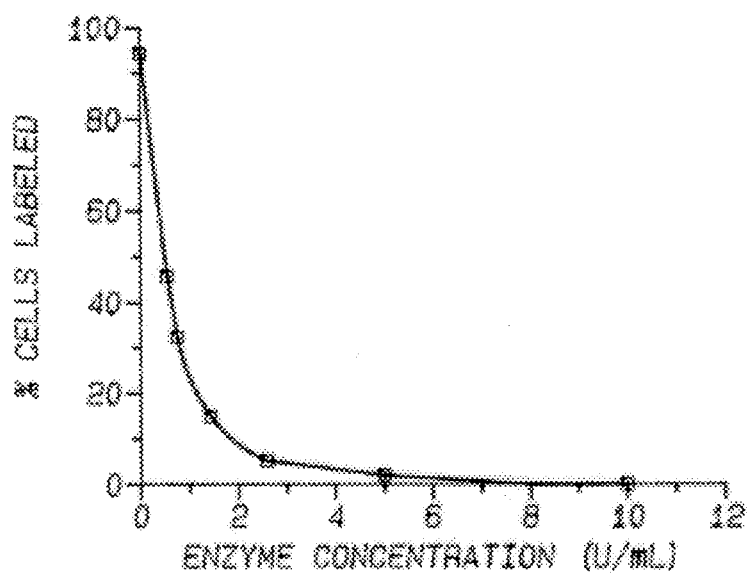
FIG. 11 is a graph of percent of FITC labelled cells as a measurement of deantigenation as a function of enzyme concentration (0.32, 0.63, 1.25, 2.50, 5.0, & 10.00), all data points are the means of three independent determinations.

Deantigenation of type B erythrocytes as a function of enzyme concentration is shown in FIG. 11. Four percent cell suspensions were incubated with X U $ml^{-1}$ of *Glycine max* enzyme in 10 mM Na citrate+300 mM glycine+1 mg $ml^{-1}$ BSA, pH 5.8, for 30 min. at 24° C. where X=0.32, 0.63, 1.25, 2.50, 5.0, & 10.00. Cells were then reacted with 1° antibody, 2° antibody FITC conjugate, and the fluorescence quantitated. At a hematocrit of 4% as little as 5.00 U $ml^{-1}$ of *Glycine max* α-D-Galactosidase completely removed the B epitope with only a 30 minute incubation at 24° C.

Figure 12:
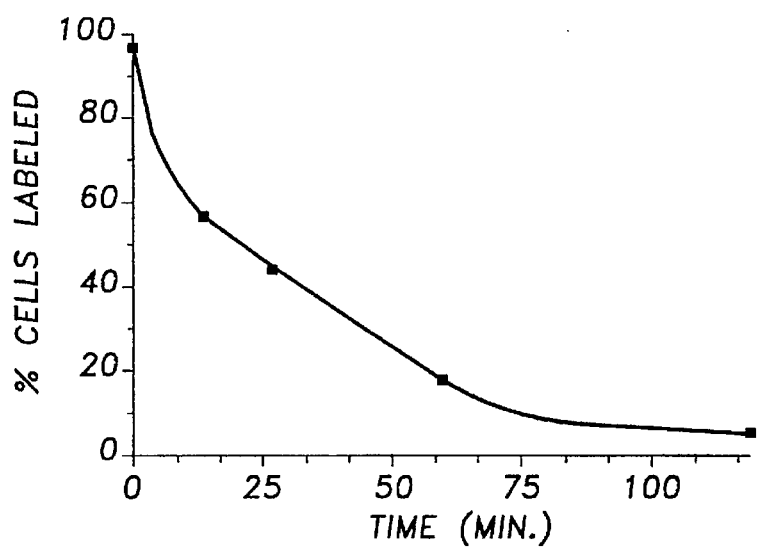
FIG. 12 is a graph of percent of FITC labelled cells as a measurement of deantigenation as a function of time (0, 15, 30, 60, 120 minutes), all data points are the means of three independent determinations.

Higher enzyme concentrations were required at higher hematocrits, however, as little as 10.00 U $ml^{-1}$ completely removed the B epitope from a 16% suspension of type B cells. At extremely low enzyme concentrations, 1.00 U $ml^{-1}$, greater than 94% of detectable fluorescence was removed from a 4% cell suspension after a two hour incubation at 24° C. (FIG. 12). Four percent cell suspensions were incubated with 0.20 U $ml^{-1}$ of *Glycine max* enzyme in 10 mM Na citrate+300 mM glycine+1 mg $ml^{-1}$ BSA, pH 5.8, for X minutes at 24° C. where X=0, 15, 30, 60, and 120 minutes. They were then reacted with 1° antibody, 2° antibody FITC conjugate, and the fluorescence quantitated.

Figure 13:
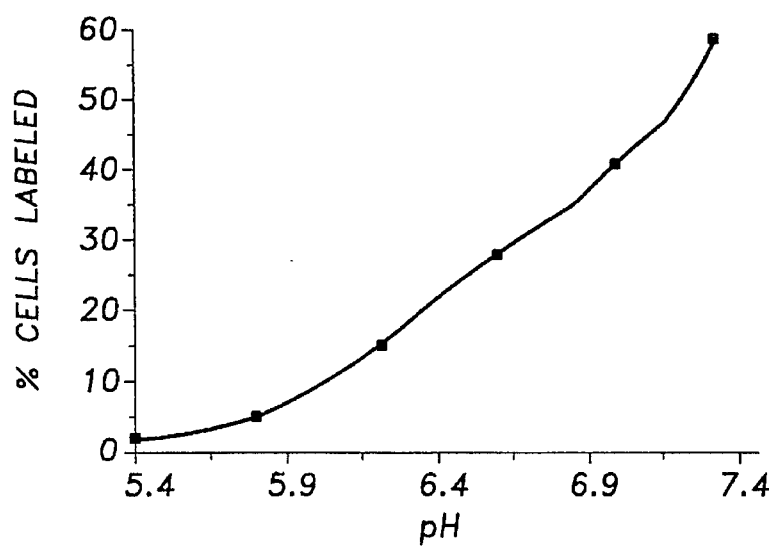
FIG. 13 is a graph of percent of FITC labelled cells as a measurement of deantigenation as a function of pH (5.4, 5.8, 6.2, 6.6, 7.0, 7.4), all data points are the means of three independent determinations.

Deantigenation as a function of pH is shown in FIG. 13. Four percent cell suspensions were incubated with 1.25 U $ml^{-1}$ of *Glycine max* enzyme in 5 mM Na citrate+5 mM Na $H_2PO_4$+300 mM glycine, pH=X, for 30 minutes at 24° C. where pH X =5.4, 5.8, 6.2, 6.6, 7.0; & 7.4. They were then reacted with 1° antibody, 2° antibody FITC conjugate, and the fluorescence quantitated. At an enzyme concentration of 1.25 U $ml^{-1}$, more than 99% of the detectable B antigen was removed at pH 5.4 with a 30 minute incubation at 24° C. Complete deantigenation could be achieved at higher pHs with higher enzyme concentrations; for example, a 16% cell suspension could be deantigenated at pH 6.2 with 10.00 U $ml^{-1}$ of enzyme.

Figure 14:
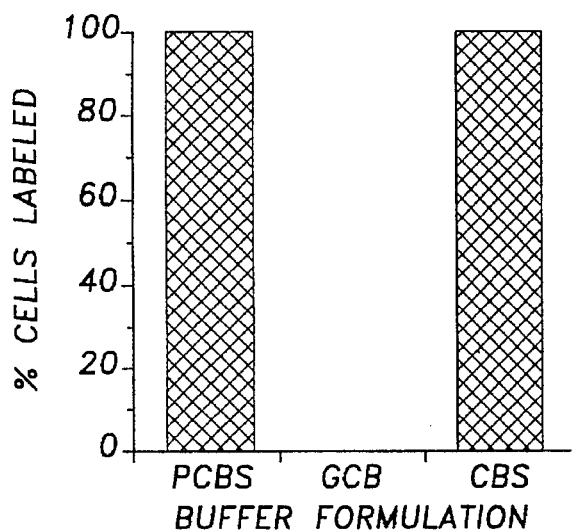
FIG. 14 is a bar graph of percent of FITC labelled cells as a measurement of deantigenation as a function of buffer composition (PCBS, GCB, CBS), all data points are the means of three independent determinations.

The effect of buffer composition was studied. FIG. 14 shows removal of the B epitope in three different buffers: PCBS (60 mM $NaH_2PO_4$+25 mM Na citrate+75 mM NaCl+1 mg $ml^{-1}$ BSA, pH 5.8), GCB (5 mM Na citrate+300 mM glycine+1 mg $ml^{-1}$ BSA, pH 5.8), or CBS (10 mM Na citrate+140 mM NaCl,+1 mg $ml^{-1}$ BSA, pH 5.8). Four percent cell suspensions were incubated with 5.0 U $ml^{-1}$ of *Glycine max* enzyme in each of the three buffers for two hours at 24° C. The cells were developed with 1° antibody, 2° antibody FITC conjugate, and the fluorescence quantitated. It was evident that at low enzyme concentrations and low hematocrits efficient deantigenation was only achieved in GCB. These findings correlated well with cell suspension studies using conventional hemagglutination assays under similar assay conditions.

Figure 15:
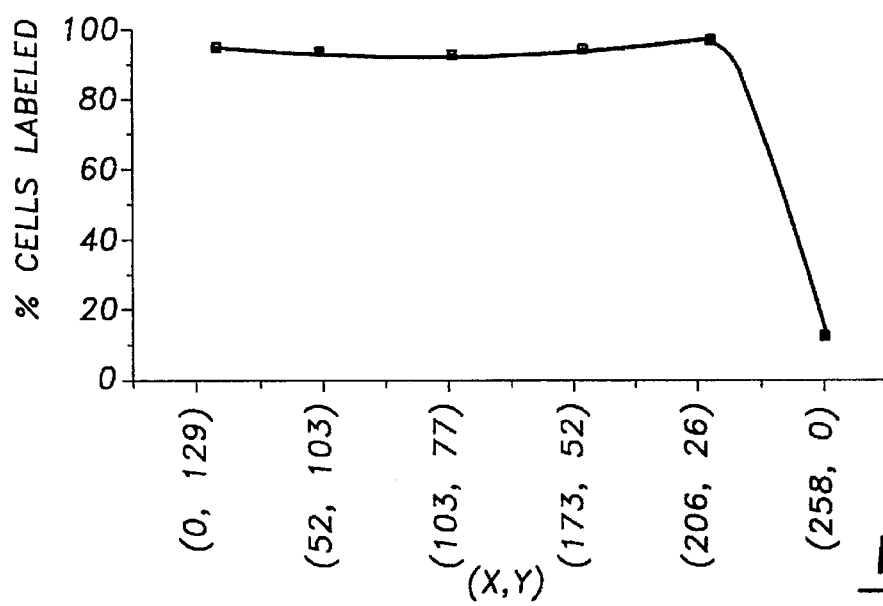
FIG. 15 is a graph of percent of FITC labelled cells as a measurement of deantigenation as a function of glycine and NaCl concentration (0,129), (52,103), (103,77), (173,52), (206,26), (258,0), all data points are the means of three independent determinations.

The effect of various isosmolal solutions of NaCl and glycine were studied, FIG. 15. Four percent cell suspensions were incubated with 1.5 U $ml^{-1}$ of Glycine max enzyme in 10 mM Na citrate+X mM glycine, +Y mM NaCl+1 mg $ml^{-1}$ BSA, pH 5.8, for 30 minutes at 24° C. where (X,Y)=(0,129), (52,103), (103,77), (173,52), (206,26), (258,0). The cells were reacted with 1° antibody, 2° antibody FITC conjugate, and then fluorescence quantitated. It was evident that increasing concentrations of NaCl inhibited deantigenation. Similar findings were confirmed in conventional hemagglutination assays.

EXAMPLE 5

CLONING AND SEQUENCING OF SOYBEAN α-D-GALACTOSIDASE

Cloning of Soybean α-D-Galactosidase:

A soybean cDNA library (a gift from Joe Polacco, University of Missouri), made in lambda ZAP (Stratagene), was screened under low stringency hybridization and wash conditions with a radiolabeled portion of the pinto bean α-D-galactosidase gene (SEQ ID No.:1) The positive clone obtained, SB-10, was excised from the lambda vector and sequenced. The deduced amino acid sequence was compared to that of the guar (Overbeek et al., 1989) and pinto bean α-D-galactosidases. SB-10 was not full length and was missing the expected 5' end of the gene, corresponding to the start codon, signal peptide, and mature N-terminus.

Modern soybean, *Glycine max*, is an allotetraploid that formed from the union of two genetically distinct species. This means that in addition to the genetic diversity bred into modern soybean for agronomic reasons, it is also likely that there are two or more different copies of the α-D-galactosidase gene in soybean in any given soybean cultivare. As with corn, soybean is a crop planted in many climates and soil conditions. Many strains exist with different characteristics for growth under these conditions. This genetic diversity may be reflected in the amino acid sequence for soybean α-D-galactosidase.

The SB-10 clone Eco RI insert was radiolabeled and used as a probe to re-screen the lambda ZAP::SB cDNA library under high stringency hybridization and wash conditions. A full length clone, SB-14a, was purified and excised. The SB-14a clone was sequenced (SEQ ID No.:2) and found to be 1750 nt in length, with a 1266 nt open reading frame encoding a protein with a 55 amino acid signal peptide (SEQ ID No.:3) and a mature length of 363 amino acids (SEQ ID No. 4). Identity of the SB-14a cDNA clone as the gene encoding soybean α-D-galactosidase was confirmed by comparison of the deduced amino acid sequence of the clone to the N-terminal and cyanogen bromide-derived peptide sequences obtained from the native soybean α-D-galactosidase. Comparison of the deduced amino acid sequence of the SB-14a clone to that of other reported α-D-galactosidases and α-N-acetylgalactosaminidases showed a high degree of sequence similarity between the different proteins.

Expression of the Soybean α-D-Galactosidase Gene in Pichia:

Active recombinant soybean α-D-galactosidase was obtained with the Pichia Expression Kit (Invitrogen) using the Pichia expression/secretion vectors pHILS1 and pPIC9. Polymerase chain reaction was used to amplify the coding region of SB-14a. The 5' PCR primer corresponded to the mature N-terminus of the protein and contained an Eco RI site designed to allow cloning of the PCR product such that the soybean ORF was in-frame with the translation start codon provided by the Pichia expression vectors. An oligo annealing to M13-pUC was used as the 3' PCR primer. The PCR product was digested with Eco RI and cloned into the Eco RI site of pHILS1 and pPCI9. The vector-insert junctions of these constructs were sequenced to determine proper ligation, orientation, and maintenance of reading frame.

Two clones, pHILS1/SB229 and pIC9/SB217, were chosen for expression in the Pichia system. Midi-prepped plasmid DNA from each clone wa linearized by Aat II/Tth 111I digestion. Pichia spheroplasts were transformed with these linear constructs. Greater than fifty His+ transformants were obtained for each construct. These were screened for the His+Mut⁻ phenotype, which indicates correct integration of the soybean construct into the yeast chromosome. Those transformants found to be correctly integrated were grown and induced on a small scale and the culture media was assayed for α-D-galactosidase activity. The transformant found to have the highest activity, pHILS1/SB229-32, was used for a medium scale induction and expression of the recombinant soybean α-D-galactosidase enzyme.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Effect of buffer composition on erythrocyte ATP, 2,3 DPG, and cholinesterase

|  | GCB | PCBS | PBS control |
|---|---|---|---|
| ATP | 98% | 116% | 100% |
| 2,3 DPG | 119% | 81% | 100% |
| cholinesterase | 102% | 87% | 100% |

B+ erythrocytes were incubated in the designated buffer. After 2 hr at 24° C., the cells were washed five times with PBS and assayed for the indicated analyte. All data points are the mean of four independent determinations and expressed as a % of the PBS buffer control.

REFERENCES

Adams, "Adenosine 5'-triphosphate determination with phosphoglycerate kinase" in *Methods of Enzymatic Analysis*, Academic Press, New York, N.Y., 539–543 (1963)

Aminoff et al., "Enzymes that destroy blood group specificity" *J. Biol. Chem.* 245:1659–1669 (1970)

Bradford, *Anal. Biochem.* 72:248–254 (1976)

Bryant, "Antibody Identification and Titration" in *An Introduction to Immunochemistry*, W. B. Sanders, Philadelphia, Pa., pp. 280–297 (1982)

Corchete et al., *Phytochemistry* 26:927–932 (1987)

Courtois & Petek, "α-galactosidase from coffee beans" *Methods in Enzymol.* 8:565–571 (1966)

Dacie et al, "The fragility of the red blood cells: its measurements and significance" *J. Path. Bact.* 46:341 (1938)

Dietz et al., "Colorimetric determination of serum cholinesterase and its genetic variants by the propionylthiocholine-dithiobis procedure" *Clin. Chem.* 19:1309–1313 (1973)

Economidou et al., "Quantitative measurements concerning A and B antigen sites" *Vox Sang.* 12:321–328 (1967)

Feinberg & Goldstein, "A Technique for Radiolabeling DNA Restriction Endonucleases to High Specific Activity, *Anal. Biochem.* 132:6–12 (1983)

Fong et al "Developmental patterns of ABO isoagglutinins in normal children correlated with the effects of age, sex, and maternal isoagglutinins" *Transfusion* 14:551–559 (1974)

Flowers et al., *Adv. Enzymol.* 48:29–95 (1979)

Goldstein et al. *Phytochemistry* 4:185–192 (1965)

Goldstein et al., "Group B erythrocytes converted to group O survive normally in A, B, and O individuals" *Science* 215:168–170 (1982)

Goldstein, "Conversion of ABO Blood Groups" *Trans. Med. Rev.* 3:206–212 (1989)

Goldstein, "The Production of Group O Cells" in *Biotechnology of Blood.* (Butterworth Heinemann, Stoneham, Ma.) pp. 75–100 (1991)

Haibach et al., "Purification and characterization of a *Coffea canephora* α-D-galactosidase isozyme" *Biochem. Biphys. Res. Comm.* 191:1564–1571 (1991)

Hanahan, "Studies on Transformation of *E. coli* with plasmids", *J. Mol. Biol.* 166:557–580 (1983)

Harlow et al., in *Antibodies*, Cold Spring Harbor Laboratory, Cold Spring Harbor, N.Y., 92–135 (1988)

Harmening, in *Modern Bloodbanking and Transfusion Practices*, F. A. Davis Company, Philadelphia, Pa., pp.80–82 (1989)

Harpaz et al., "Studies on B-antigenic sites of human ertyrocytes by use of coffee bean α-galactosidase", *Arch. Biochem. Biphys.* 170:676–683 (1975)

Harpaz et al., "α-D-galactosidase from soybeans destroying blood group B antigens" *Eur. J. Biochem.* 77:419–426 (1977)

Hata et al., *Biochem. Intl.* 28:77–86 (1992)

Hobbs et al., "An ELISA for blood group specific exoglycosidases" *J. Immunol. Methods.* 160:261–266 (1993)

Honda et al., "Enzymic synthesis of galactooligosaccharides by trans-glycosylation with thermostable α-galactosidase from *Pyconporus cinnabarinus*" Saga Daigaku Nogakubu Iho. 69:55–61 (1990)

Hoskins et al., "Mucin degradation in human colon ecosystems. Isolation and properties of fecal strains that degrade ABH blood group and oligosaccharides from mucin glycoproteins" *J. Clin. Invest.* 75:944–953 (1987)

Issit, "Forces That Hold Red Cells Apart" in *Applied Blood Group Serology*, Montgomery (Scientific Publications, Miami, Fla.) pp. 35–36 (1985)

Kitahata et al. "Synthesis of 6-O-α-D-galactosyl α-cyclodextrin by coffee bean α-galactosidase" *Biosci. Biotechnol. Biochem.* 56:1518–1519 (1992)

Kubo, "Changes in the specificity of blood groups induced by enzymes from soil fungi" *J. Forensic Sci.* 34:96–104 (1989)

Laemmli "Cleavage of structural proteins during the assembly of the head of bacteriophage T4" *Nature* 227:680–685 (1970)

Landsteiner, "Uber agglutination-serscheinungen normalen menschlichen blutes" *Klin. Wschr.* 14:1132 (1901)

Lenny et al., in *Biotechnology of Blood* (Butterworth-Heinemann, Boston, Mass.) pp. 75–100 (1991)

Lenny et al., "Group B.ertyrocytes enzymatically converted to group O survive normally in A, B, and O individuals" *Science* 245:168–170 (1982)

Lenny et al., "Single-unit transfusions of RBC enzymatically converted from group B to group O to group A and O normal volunteers" *Blood* 77:1383–1388 (1991)

Levy et al., "The α-N-acetylgalactosaminidase (A-xyme) from *Clostridium perfringens*" *Fed. Proc.* 37:1601 (1978)

Levy et al., "Purification and properties of α-N-acetylgalactosaminidase from *Clostridum perfringens*" *Biol. Chem.* 255:11737–11742 (1980)

Mawhinney, *J. Chromatogr.* 351:91–102 (1986)

Mizutani et al., "Visual disturbances, serum glycine levels and transurethral resection of the prostate", *J. Urol.* 144:697–699 (1990)

Mollison et al., in *Blood Transfusion in Clinical Medicine*. Blackwell Scientific Publications, Oxford, England, p. 593 (1987)

Moore et al. "A modified ninhydrin reagent for the photometric determination of amino acids and related compounds", *J. Bio. Chem.* 211:907–913 (1954)

Moran & Walker "Molecular Cloning of Two Novel Protein Kinase Genes from Arabidopsis, *Anal. Biochem.* 132:6–12 (1993)

Overbeek et al. "Cloning and Nucleotide Sequence of the α-Galaltosiotse cDNA from Cyamopsis Tetragonoluba (Gurr) *Plant Mol. Bioi.* 13:541–550 (1989)

Rose et al., "Direct determination of 2,3-diphosphoglycerate" *Anal. Biochem.* 35:177–180 (1970)

Romano et al., "Red cell destruction in vivo by low concentrations of IgG anti-A" *Br. J. Haematol* 29:121–127 (1987)

Sambrook et al., *Molecular Cloning: A Lab. Manual*, Cold Spring Harbor Press (1989)

Schmidt, in: *Immunobiology of the Erythrocyte*, Alan R. Liss Inc., New York, N.Y., pp.251–261 (1980)

Sharon & Fibach, "Quantitative Flow Cytometric Analysis of ABO Red Cell Antigens" *Cytometry* 12:545–549 (1991)

Sherwood et al., "Assay of plasma glycine by HPLC with electrochemical detection in patients undergoing glycine irrigation during gynaecological surgery", *Clinica Chimica Acta* 203:275–283 (1991)

Srivastava et al., "α-L-fucosidase from bull seminal plasma: its purification and acrosome reaction promoting property" *Biochem. Biophyso Res. Commun.* 137:1061–1068 (1986)

Tsuji et al., "Purification and characterization of α-L-fucosidase from *Bacillus circulans* grown on porcine gastric mucin" *J. Biochem.* 107:324–330 (1990)

Wantanabe et al., *J. Exp.Med.* 144, 644–653 (1976)

Yatziv et al., "Action of α-galactosidase on glycoprotein from human B-erythrocytes", *Biochem. Biophys. Res. Commun.* 45:514–518 (1971)

We claim:

1. A method of preparing deantigenated erythrocytes including the steps of isolating erythrocytes of a defined blood type;

suspending the isolated erythrocytes in zwitterionic buffer wherein the zwitterionic buffer consists essentially of 0.1 to 20 mM Na titrate, 220 to 440 mM glycine or alanine and 0.01 to 30 mg ml$^{-1}$ albumin at pH 5.8;

adding a multimeric eucaryotic exoglycosidase with multiple subunits selected to act on the isolated erythrocytes;

incubating at 24° C. for between one and two hours; and washing in phosphate buffered saline.

2. A method according to claim 1 wherein the erythrocytes are selected from the group consisting of blood types $A_2$, B and $A_2B$.

3. A method according to claim 1 wherein the zwitterionic buffer consists of 5 mM Na citrate, 300 mM glycine and 1 mg ml$^{-1}$ albumin at pH 5.8.

4. A method according to claim 1 wherein the erythrocytes express B antigen and the exoglycosidase is *Glycine max* α-D-galactosidase.

5. A method according to claim 1 wherein the erythrocytes express $A_2$ antigen and the exoglycosidase is *Gallus domesticus* α-N-acetyl-galactosaminidase.

6. A deantigenation buffer consisting of 0.1 to 20 mM Na citrate, 220 to 440 mM glycine and 0.1 to 30 mg ml$^{-1}$ albumin at pH 5.8.

7. A deantigenation buffer according to claim 6 consisting of 5 mM Na citrate, 300 mM glycine and 1 mg ml$^{-1}$ albumin at pH 5.8.

* * * * *